United States Patent [19]

Wright et al.

[11] Patent Number: 4,954,416
[45] Date of Patent: Sep. 4, 1990

[54] TETHERED SULFONIUM SALT PHOTOINITIATORS FOR FREE RADICAL POLYMERIZATION

[75] Inventors: Bradford B. Wright, North St. Paul; Robert J. DeVoe, St. Paul, both of Minn.

[73] Assignee: Minnesota Mining and Manufacturing Company, St. Paul, Minn.

[21] Appl. No.: 287,909

[22] Filed: Dec. 21, 1988

[51] Int. Cl.$^5$ .................... G03C 1/78; G03C 5/00; C08F 2/50
[52] U.S. Cl. .................... 430/281; 430/288; 430/325; 430/916; 430/921; 522/14; 522/15; 522/25; 522/31; 502/168
[58] Field of Search ............ 522/14, 15, 31, 25; 430/281, 916, 921, 325, 288, 271

[56] References Cited

U.S. PATENT DOCUMENTS

| | | | |
|---|---|---|---|
| 4,069,054 | 1/1978 | Smith | 96/115 |
| 4,245,029 | 1/1981 | Crivello | 430/280 |
| 4,250,053 | 2/1981 | Smith | 252/426 |
| 4,256,828 | 3/1981 | Smith | 430/280 |
| 4,423,136 | 12/1983 | Crivello et al. | 430/281 |
| 4,610,952 | 9/1986 | Crivello | 430/325 |
| 4,684,671 | 8/1987 | Tsuchiya et al. | 522/31 |
| 4,735,632 | 4/1988 | Oxman et al. | 51/295 |

FOREIGN PATENT DOCUMENTS 61-212555 9/1986 Japan .

OTHER PUBLICATIONS

Pappas, S. P., *Prog. Org. Coatings,* 1985, 13, 35.
Crivello, J. V., *Polym. Eng. Sci.,* 1983, 23, 953.
Kondo, S., Muramatsu, M., Tsuda, K., *J. Macromol. Sci. Chem.,* 1983, 19, 999.
Pappas, S. P., *Radiat. Phys. Chem., 1985, 25, 633.*
Hagemann, H. J. *Prog. Org. Coat.,* 1985, 13, 123.
Crivello, J. V., *Adv. Polym. Sci.,* 1984, 62, 1.
Baumann, H., Timpe, H.-J., Bottcher, H., *Z. Chem.,* 1983, 23, 394 (English translation provided).
Timpe, H.-J., Bah, A., *Makromol. Chem. Rapid Commun.,* 1987, 8, 353 (English translation provided).
Closs, G. L., Miller, J. R., *Science,* 1988, 240, 440.
Oevering, H., Paddon-Row, M. N., Heppener, M., Oliver, A. M., Cotsaris, E., Verhoeven, J. W., Hush, N. S., *J. Am. Chem. Soc.,* 1987, 109, 3258.
Crivello, J. V., Lam, J. H. W., *J. Polym. Sci.: Polymer Chemistry,* Ed. 1980, 18, 2677.
Saeva, F. D., *Tetrahedron,* 1986, 42, 6123.
K. Ichimura, A. Kameyama, K. Hayashi, *J. Appl. Polym. Sci.,* 1987, 34, 2747.

*Primary Examiner*—Paul R. Michl
*Assistant Examiner*—Christopher D. RoDee
*Attorney, Agent, or Firm*—Donald M. Sell; Walter N. Kirn; Lorraine R. Sherman

[57] ABSTRACT

Free radical polymerizable compositions contain a sulfonium salt which is tethered to at least one of an electron donor and a sensitizer, and a polymerizable monomer, demonstrate substantially enhanced photosensitivity. This invention also provides layered structures comprising a substrate coated with a free radical polymerizable composition containing a sulfonium salt which is tethered to at least one of an electron donor and a sensitizer, and the polymerized layered structures. A method for the preparation of certain tethered sulfonium salts is described.

17 Claims, No Drawings

TETHERED SULFONIUM SALT PHOTOINITIATORS FOR FREE RADICAL POLYMERIZATION

FIELD OF THE INVENTION

This invention relates to free radical polymerization of monomers using sensitized triarylsulfonium salt photoinitiators. In another aspect, a method of preparing novel amino-substituted triarylsulfonium salts is disclosed.

BACKGROUND OF THE INVENTION

Electron transfer sensitization of triarylsulfonium salts for radical curing has been known and practiced in the art (see Pappas, S. P., *Prog. Org. Coatings* 1985, 13, 35; Crivello, J. V. *Polym. Eng. Sci.* 1983, 23, 953; Kondo, S.; Muramatsu, M.; Tsuda, K. *J. Macromol. Sci. Chem.* 1983, 19, 999; Pappas, S. P. *Radiat. Phys. Chem.* 1985, 25, 633; Hagemann, H. J. *Prog. Org. Coat.* 1985, 13, 123; Crivello, J. V. *Adv. Polym. Sci.* 1984, 62, 1; Baumann, H.; Timpe, H.-J.; Bottcher, H. *Z. Chem.* 1983, 23, 394; Timpe, H.-J.; Bah, A. *Makromol. Chem. Rapid Commun.* 1987, 8, 353). A three component photoinitiator system comprised of an electron donor, sensitizer, and electron accepting initiator has been taught in U.S. Pat. No. 4,735,632.

Photosensitive tethered donor-acceptor compounds have been described in the art as model systems for the study of electron transfer (Closs, G. L.; Miller, J. R. *Science* 1988, 240, 440; Oevering, H.; Paddon-Row, M. N.; Heppener, M.; Oliver, A. M.; Cotsaris, E.; Verhoeven, J. W.; Hush, N. S. *J. Am. Chem. Soc.* 1987,109, 3258). Tethered alkyldiarylsulfonium salts useful in photocuring of cationically polymerizable monomers are known (see U.S. Pat. Nos. 4,250,053, and 4,069,054). The greater stability of triarylsulfonium salts over sulfonium salts with one or more alkyl groups attached directly to sulfur is known (see Crivello, J. V.; Lam, J. H. W. *J. Polym. Sci.: Polymer Chemistry Ed.* 1980, 18, 2677; Saeva, F. D. *Tetrahedron* 1986, 42, 6123).

A method for preparation of alkoxy/aryloxy substituted triarylsulfonium salts using alcohols and fluoro-substituted sulfonium salts has been described (see Japanese Patent 61-212555); however, no mention was made regarding reaction with primary or secondary amines.

SUMMARY OF THE INVENTION

Briefly, this invention provides free radical polymerizable compositions comprising an ethylenically unsaturated monomer, at least one of an electron donor and sensitizer, and a triarylsulfonium salt, wherein at least one of an electron donor and sensitizer is tethered with the triarylsulfonium salt through one or more covalent chemical bonds.

This invention provides free radical polymerizable compositions of substantially increased photosensitivity comprised of an ethylenically unsaturated monomer, at least one of an electron donor and a sensitizer, and a triarylsulfonium salt wherein at least one of the electron donor and sensitizer is tethered with the sulfonium salt through one or more covalent chemical bonds. More specifically, this invention teaches that an electron donor and/or sensitizer tethered to a triarylsulfonium salt has a synergistic effect on the photosensitization of free radical initiation of polymerizable compositions compared to that of an untethered composition. Furthermore, tethered compositions of this invention demonstrate excellent thermal stability in contrast to known diaryliodonium salt/amine complexes (see K. Ichimura, A Kameyama, K. Hayashi *J. Appl. Polym. Sci* 1987, 34, 2747).

The tether may be composed of any arrangement of atoms provided that the tether contains a tetracoordinate carbon within the backbone of the tether. Synthesis of the tether necessarily varies depending on the nature of its structure.

In another aspect this invention relates to layered structures comprising a substrate coated on at least one surface thereof with a free radical polymerizable composition comprising a monomer and at least one of 1) a sulfonium salt which is tethered to an electron donor and optionally a sensitizer, and 2) a sulfonium salt tethered to a sensitizer and optionally an electron donor, and to the polymerized layered structures. The layered structures can comprise a substrate having overcoated on at least a portion of the substrate surface a polymerizable composition.

There is further provided a graphics article which is a layered structure comprising the composition described above in the form of a coating on a substrate which provides for the formation of images.

In a still further aspect of this invention there is provided a method for preparing novel mono-N- or di-N,N-alkylaminoarylenediarylsulfonium salts and mono-N-or di-N,N-arylaminoarylenediarylsulfonium salts and N-alkyl-N-arylaminoarylenediarylsulfonium salts comprising the steps of:

(a) reacting an admixture comprising a p-fluorophenyldiphenylsulfonium salt with a primary or secondary amine in a provided solvent (such as dimethyl sulfoxide (DMSO)) at 40°-60° C., and (b) isolating the resultant amino-substituted sulfonium salt.

Tethered sulfonium salt photoinitiators, with demonstrated utility in curing free radically polymerizable compositions as described in the embodiments of this invention are novel in the art. What the prior art has not shown, but this invention teaches is that compositions which contain a free radically polymerizable monomer and triarylsulfonium salts which are tethered to electron and/or sensitizers cure more rapidly than the corresponding untethered composition. The tethered sulfonium salt-containing compositions of the invention surprisingly show superior rates of cure compared to compositions using even greater amounts of untethered sulfonium salt initiator. In addition, compositions of the present invention possess superior thermal stability.

In this application:

"tethered" means the connection of two moieties by means of a chain of one or more atoms;

"photocuring" means photopolymerizing, curing, hardening, gelling, or polymerizing the free radically polymerizable compositions of this invention in the presence of actinic radiation;

"mask" means any device used to shield, i.e., will not allow actinic radiation to pass through those selected portions of a substrate during irradiation, and hence, a polymerization process;

"substrate" means those materials which will maintain their integrity under the conditions imposed upon them during the coating of polymerizable compositions of this invention as thin organic coatings and overcoatings and polymerization of the resultant compositions;

"tetracoordinate" means bonded to four separate substituents, wherein the substituents may be the same or different; and $E_{ox}$ means oxidation potential;

$E_{red}$ means reduction potential; and $E_{o,o}$ means energy of the electronic excited state.

The terms sensitizer and photosensitizer are used interchangeably throughout.

The terms initiator and photoinitiator are used interchangeably throughout.

Compositions of this invention find use in protective coatings, photopolymers, graphic arts, especially in the art of printing plates, and wherever free radical polymerization of photocurable compositions is desirable.

DETAILED DESCRIPTION AND SPECIFICATION OF THE INVENTION

This invention teaches the photopolymerization of free radically polymerizable compositions by a photoinitiator comprising a triarylsulfonium salt, at least one of a sensitizer and an electron donor, wherein at least one of the electron donor (embodiment 1) and the sensitizer (embodiment 2) is tethered to the triarylsulfonium salt. When a donor is tethered to the sulfonium salt it is preferred that a sensitizer be present also. When a sensitizer is tethered to the sulfonium salt, it is preferred that a donor be present also. In some cases, the donor, sensitizer, and sulfonium salt will all be part of the same molecule. In such cases, a tether can be to the donor group or to the sensitizer group or tethers can be to both donor and sensitizer groups.

Tethered sulfonium salt photoinitiators of this invention can be represented by two general formulae:

General formula (1) is represented by:

$$S^+(A^1)_m(A^2-T-Q)_n X^- \quad (1)$$

wherein $S^+$ is a positively charged sulfur atom, $A^1$ is an aryl group having 6 to 50 carbon atoms which can be substituted by 1 to 5 substituents chosen from alkyl, haloalkyl, haloaryl, alkoxy, aralkyl, alkaryl, aryloxy, thioalkyl, thioaryl groups of 1-18 carbon atoms; carboxyl, carboxaldehyde, carboxylic acid esters of alcohols of 1-18 carbons, and carboxylic acid amides of amines of 1-18 carbons.

$A^2$ is an arylene group having 6 to 50 carbon atoms which can be substituted by 1 to 4 substituents chosen from alkyl, haloalkyl, haloaryl, alkoxy, aralkyl, alkaryl, aryloxy, thioalkyl, thioaryl groups of 1-18 carbon atoms; carboxyl, carboxaldehyde, carboxylic acid esters of alcohols of 1-18 carbons, and carboxylic acid amides of amines of 1-8 carbons, which is connected to Q through the tether T, m=0, 1, or 2, n=1, 2, or 3 with the proviso that n+m=3

T represents the tether which joins the triaryl sulfonium salt moiety to Q and contains at least one tetracoordinate carbon atom. Preferably, T is chosen from divalent groups such as alkylene, aminoalkylene, aralkylene, alkarylene, haloalkylene, thioalkylene, oxyalkylene, wherein the divalent group contains 1 to 40 C atoms, and none or 1 to 10 N, 0, S, P, Si, and Se heteroatoms, and may contain amide, ester, ether, or ketone functionality along the backbone, with the proviso that every path from $A^2$ to Q contains at least one tetracoordinate carbon atom, and $X^-$ is a counterion, and Q represents an electron donor.

Q, the electron donor, can be any group capable of donating at least one electron. In some instances the electron donor Q is a photosensitizer. By photosensitizer is meant a group or compound which in an excited state is capable of donating an electron to a sulfonium group.

General formula 2 is represented by:

$$(Q-T)_k A^2 S^{+A3} (T-Q)_j X^- \quad (2)$$

wherein $S^+$, $A^2$, T, $X^-$ and Q are as defined above;

$A^3$ represents a substituted or unsubstituted polycyclic group comprising at least two distinct fused or single phenyl rings, wherein two phenyl rings are singly and individually bonded to $S^+$;

j=0, 1, 2, 3, 4; and k=0, 1, 2;

with the proviso that j+k >1.

Preferably, $A^3$ represents a polycyclic group having 2 to 4 rings that can be substituted by one or more alkyl, aryl, aralkyl, alkaryl, alkoxy, carboalkoxy, amido, thioalkyl, thioaryl, aryloxy, and acyl groups having up to carbon atoms; cyano, nitro, sulfonato, sulfonyl, and sulfonoxy groups; and halogen.

Two preferred embodiments of the invention can be represented by the formulae below:

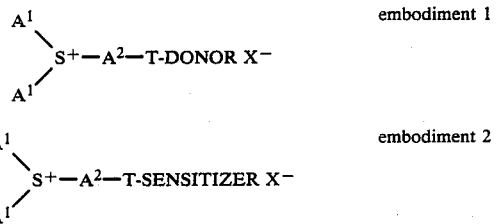

embodiment 1 embodiment 2 wherein $S^+$, $A^1$, $A^2$ and T are as previously defined, DONOR represents an electron donor, and SENSITIZER represents a sensitizer. In the first embodiment the triarylsulfonium salt bears a substituent which is a tether attached to an electron donor. In the second embodiment the triarylsulfonium salt bears a substituent which is a tether attached to a sensitizer.

Preferably, the tether can be chosen from divalent groups such as alkylene, aminoalkylene, aralkylene, alkarylene, haloalkylene, thioalkylene, oxyalkylene, wherein the divalent group contains 1 to 40 C atoms, and none or 1 to 10 N, 0, S, P, Si, and Se heteroatoms, and may contain amide, ester, ether, or ketone functionality along the backbone. The tether can be unsubstituted or substituted with one or more non-interfering substituents. By non-interfering substituents is meant any substituent which will not have a more negative reduction potential than the sulfonium salt moiety. Examples of such substituents include unsubstituted alkoxy and alkyl groups of any chain length. The term backbone refers to the longest continuous chain of atoms connecting the electron donor to the sulfonium salt or the sensitizer to the sulfoniux salt.

Suitable groups A can be independently chosen from phenyl, naphthyl, biphenyl, henanthryl, pyrenyl, and anthracenyl, each of which can bear from 1 to 5 substituents chosen from alkyl, haloalkyl, haloaryl, alkoxy, aralkyl, alkaryl, aryloxy, thioalkyl, thioaryl groups of 1–18 carbon atoms; carboxyl, carboxaldehyde, carboxylic acid esters of alcohols of 1–18 carbons, and carboxylic acid amides of amines of 1–18 carbons.

Suitable groups $A^2$ can be divalent arenes derived from benzene, naphthalene, biphenyl, phenanthrene, pyrene, anthracene, all can bear from 1 to 4 substituents chosen from alkyl, haloalkyl, haloaryl, alkoxy, aralkyl, alkaryl, aryloxy, thioalkyl, thioaryl groups of up to 18 carbon atoms; carboxyl, carboxaldehyde, carboxylic acid esters of alcohols of 1–18 carbons, carboxylic acid amides of amines of 1–18 carbons.

Counterion $X^-$ preferably can be fluoride, chloride, bromide, iodide, hexafluorophosphate, hexafluoroantimonate, hexafluoroarsenate, tetraarylborates, tetrafluoroborates, sulfate, nitrate, phosphate, hydroxypentafluoroantimonate, methanesulfonate, trifluoromethanesulfonate, p-toluenesulfonate, or any other negatively charged species which does not inhibit free radical polymerization.

Triarylsulfonium salt photoinitiators which are tethered (the tether is represented by T in the structures below) to more than one donor, more than one sensitizer, or a combination thereof can show similar enhanced activity as a free radical photoinitiator. Examples include:

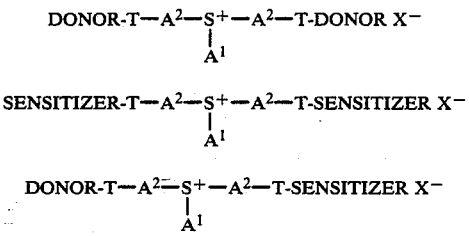

wherein $S^+$, X, T, Ar, $A^1$, $A^2$, SENSITIZER, and DONOR are as defined above.

Suitable electron donors have $E_{ox}$ greater than zero and less than or equal to $E_{ox}$ of 1,4-dimethoxybenzene. Preferably $E_{ox}$ of the donor is between 0.5 and 1.0 volts vs. a saturated calomel electrode ("S.C.E."). $E_{ox}$ donor values can be determined experimentally or obtained from references such as "Technique of Electroorganic Synthesis Part II techniques of Chemistry", N. L. Weinburg, Ed., Vol. V, 1975; and C. K. Mann and K. K. Barnes, "Electrochemical Reactions in Nonaqueous Systems", 1970. Preferred donors which are commercially available or known in the art include compounds and groups such as amines (including aminoaldehydes and aminosilanes), amides (including phosphoramides), ethers (including thioethers), ureas (including thioureas), ferrocene, sulfinic acids and their salts, salts of ferrocyanide, ascorbic acid and its salts, dithiocarbamic acid and its salts, salts of xanthates, salts of ethylenediamine tetraacetic acid and salts of tetraphenylboronic acid. Salts of the above donors may include the triarylsulfonium initiator to which it is tethered in the form of a betaine (internal salt). The donor can be unsubstituted or substituted with one or more non-interfering substituents.

Preferred amine donors include alkyl-, aryl-, alkaryl-, and aralkyl-amines. The amines can be primary, secondary, and tertiary amines such as methylamine, ethylamine, propylamine, butylamine, triethanolamine, amylamine, hexylamine, 2,4-dimethylaniline, o-, m-, p-toluidine, benzylamine, aminopyridine, N,N'-dimethylethylenediamine, N,N'-diethylethylenediamine, N,N'-dibenzylethylenediamine, N,N'-diethyl-1,3-propanediamine, N,N'-diethyl-2-butene-1,4-diamine, N,N'-dimethyl-1,6-hexanediamine, piperazine, 4,4'-trimethylenepiperidine, 4,4'-ethylenedipiperidine, p-N,N-dimethylaminophenethanol and p-N,N-dimethylaminobenzonitrile; aminoaldehydes such as p-N,N-dimethylaminobenzaldehyde, p-N,N-diethylaminobenzaldehyde, 9-julolidinecarboxaldehyde, and 4-morpholinobenzaldehyde; and aminosilanes such as trimethylsilylmorpholine, trimethylsilylpiperidine, bis(dimethylamino)diphenylsilane, tris(dimethylamino)methylsilane, N,N-diethylaminetrimethylsilane, tris(dimethylamino)phenylsilane, tris(methylsilyl)amine, tris(dimethylsilyl)amine, bis(dimethylsilyl)amine, N,N-bis(dimethylsilyl)aniline, N-phenyl-N-dimethylsilyl-aniline, and N,N-dimethyl-N-dimethylsilylamine.

Preferred amide donors include N,N-dimethylacetamide, N,N'-diethylacetamide, N-methyl-N-phenylacetamide, hexamethylphosphoramide, hexaethylphosphoramide, hexapropylphosphoramide, trimorpholinophosphine oxide, and tripiperidinophosphine oxide.

Suitable ether donor compounds include 4,4'-dimethoxybiphenyl, 1,2,4-trimethoxybenzene, and 1,2,4,5-tetramethoxybenzene.

Suitable urea donor compounds include N,N'-dimethylurea, N,N-dimethylurea, N,N'-diphenylurea, tetramethylthiourea, tetraethylthiourea, tetra-n-butylthiourea, N,N-di-n-butylthiourea, N,N'-di-n-butylthiourea, N,N-diphenylthiourea, and N,N'-diphenyl-N,N'-diethylthiourea.

Preferred sensitizers, which are commercially available or known in the art, vary with the nature of substitution on the sulfonium salt and fulfill the requirements of the following equation: $E_{red}$ (sulfonium salt) $< E_{ox}$ (sensitizer) $-E_{o,o}$ (sensitizer) where $E_{ox}$ (sulfonium salt) is the reduction potential for the sulfonium salt to be employed, $E_{o,o}$ (sensitizer) and $E_{ox}$ (sensitizer) are the energy of the lowest excited state and the oxidation potential of the sensitizer, respectively. Reduction and oxidation potentials can be measured by those skilled in the art and as described previously and may vary up to plus or minus 0.2 V according to experimental conditions if the reduction or oxidation occurs in an irreversible manner (see J. Heinze Angew. Chem. Int. Ed. Eng. 1984, 23, 831). All electrochemical potentials measured in the preceding equation are to be measured relative to the same standard electrode. $E_{o,o}$ for singlet and triplet lowest excited states can be determined, for example, from the 0,0 emission bands observed in the fluorescence or phosphorescence emission spectra, respectively, (Cowan, D. 0.; Drisko, R. L. "Elements of Organic Photochemistry", Plenum, New York, 1976). Suitable sensitizers absorb radiation in the wavelength range of 300 to 700 nm. Preferably, $E_{ox}$ (sensitizer)-$E_{o,o}$ (sensitizer) is in the range of $-1.5$ electron to $-4.5$ electron V vs. S.C.E.

Sensitizers include compounds and groups in the following categories: ketones, coumarin dyes, xanthene dyes, acridine dyes, thiazole dyes, thiazine dyes, oxazine dyes, azine dyes, aminoketone dyes, porphyrins, aromatic polycyclic hydrocarbons, aromatic polycyclic hydrocarbons with one or more heterocyclic components, p-substituted aminostyrylketone compounds, aminotriarylmethanes, merocyanines, squarylium dyes, and pyridinium dyes. Preferable sensitizers are 4-piperazinoacetophenone, 4,4'-bis(dimethylaminobenzylidene)acetone, 1,2,4,5,3H,6H,10H-tetrahydro-9-carboethoxy[1]benzopyrano(9,9a,1-gh)quinolizin-10-one, perylene, and carbazole.

Tethered sulfonium salt photoinitiators of this invention are prepared by two methods.

In one method, similar to the method taught in Japanese Patent No. 61-212555, fluorinated triaryl sulfonium salt of formula p-$(FA^2)_nS^+(A^1)_mX^-$, wherein $S^+$, $A^1$, $A^2$, $X^-$, $n$, and $m$ are as previously defined, is condensed with up to n donors and/or sensitizers bearing a tether with nucleophilic functionality such as hydroxy, thiol, primary or secondary amine, alkoxide, phenolate, and thiolate.

Suitable fluorinated triarylsulfonium salts are typically salts of sulfonium cations such as p-fluorophenyl diphenyl sulfonium, bis(p-fluorophenyl) phenyl sulfonium, and tris(p-fluorophenyl) sulfonium and the like. Suitable donors and sensitizers bearing a tether with nucleophilic functionality are, for example, N-methylpiperazine, 4-piperazinoacetophenone, and p-hydroxyethyl-N,N-diethylaniline.

The condensation is typically accomplished by mixing 1 equivalent of fluorinated triarylsulfonium salt with 1 to 10 equivalents of donor and/or sensitizer bearing a tether with nucleophilic functionality in a dipolar aprotic solvent such as dimethyl sulfoxide, N,N-dimethylformamide, and hexamethylphosphorus triamide, and the like, and subsequent heating, preferably at 40° C. to 100° C. for 0.1 to 72 hours. Isolation is generally accomplished by pouring the reaction mixture into water and adding an aqueous solution containing the salt of an anion, such as ammonium hexafluorophosphate, and ammonium hexafluorostibnate, which generates an aqueous insoluble salt of the triarylsulfonium cation. The solid triarylsulfonium salt is collected by extraction into an organic liquid in which it is soluble, such as dichloromethane, drying over a drying agent such as anhydrous magnesium sulfate, filtering off the magnesium sulfate, and evaporation of the organic solvent.

In a second method, typically 1 equivalent of a substituted or unsubstituted diaryl sulfoxide (such as diphenyl sulfoxide, and ditolyl sulfoxide) is treated with a donor and/or sensitizer which is bound to an activated aromatic nucleus in a Friedel-Crafts substitution reaction. The condensation is carried out typically in methanesulfonic acid according to the method described in U.S. Pat. No. 4,451,408. Isolation is generally accomplished by pouring the reaction mixture into water and adding an aqueous solution containing the salt of an anion, such as ammonium hexafluorophosphate, and ammonium hexafluorostibnate, which generates an aqueous insoluble salt of the triarylsulfonium cation. The solid triarylsulfonium salt is collected by extraction into an organic liquid in which it is soluble, such as dichloromethane, drying over a drying agent such as anhydrous magnesium sulfate, filtering off the magnesium sulfate, and evaporation of the organic liquid under reduced pressure.

Suitable polymerizable monomers are well known in the art and contain at least one ethylenically-unsaturated double bond and can be oligomers which are capable of undergoing free radical polymerization. Such monomers include mono-, di-, or polyacrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethylene glycol diacrylate, diethylene glycol diacrylate, triethylene glycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, bis[1-(2-acryloxy)]-p-ethoxyphenyldimethylmethane, bis[1-(3-acryloxy-2-hydroxy)]-propoxyphenyldimethylmethane, tris(hydroxyethyl)isocyanurate trimethacrylate, glycidyl methacrylate, hydroxyethyl methacrylate; the bisacrylates and bismethacrylates of polyethylene glycols of molecular weight 200–500, copolymerizable mixtures of acrylated monomers such as those of U.S. Pat. No. 4,652,274, and acrylated oligomers such as those of U.S. Pat. No. 4,642,126; unsaturated amides such as methylene bis(methacrylamide), 1,6-hexamethylene bis(acrylamide), diethylenetriamine tris(acrylamide), N-vinylpyrrolidone and beta-methacrylaminoethyl methacrylate; and vinyl compounds such as styrene, diallyl phthalate, divinyl succinate, divinyl adipate, and divinyl phthalate. Mixtures of two or more monomers can be used.

TABLE I

Structure and Naming of Sulfonium and Iodonium Salts*

| STRUCTURE | NUMBER |
|---|---|
| φ\S+—⟨O⟩—CH₂CH₂NH₂ PF₆⁻ (with second φ/) | I |
| φ\S+—⟨O⟩—CH₂CH₂NHC(=O)—⟨O⟩—NMe₂  PF₆⁻ | II |
| φ\S+—⟨O⟩—OCH₂C(=O)NH(CH₂)₃NMe₂ PF₆⁻ | III |

TABLE I-continued
Structure and Naming of Sulfonium and Iodonium Salts*

| STRUCTURE | NUMBER |
|---|---|
| φ−S+(φ)−C₆H₄−OCH₂C(O)NH(CH₂)₂NMe₂ PF₆⁻ | IV |
| φ−S+(φ)−C₆H₄−OCH₂C(O)NH(CH₂)₆NMe₂ PF₆⁻ | V |
| φ−S+(φ)−C₆H₄−OCH₂C(O)NH(CH₂)₆NMe₂ PF₆⁻ | VI |
| φ−S+(φ)−C₆H₄−F PF₆⁻ | VII |
| φ−S+(φ)−C₆H₄−N(piperidine) PF₆⁻ | VIII |
| φ−S+(φ)−C₆H₄−N(piperazine)N−C₆H₄−C(O)CH=CH−C₆H₄−NMe₂ PF₆⁻ | IX |
| φ−S+(φ)−C₆H₄−N(piperazine)N−C₆H₄−C(O)CH₃ PF₆ | X |
| φ−S+(φ)−C₆H₄−NH(CH₂)₄NMe₂ PF₆⁻ | XI |
| φ−S+(φ)−C₆H₄−N(piperazine)NCH₃ PF₆⁻ | XII |
| φ−S+(φ)−C₆H₄−N(piperazine)N−CH₂−(anthracenyl) PF₆⁻ | XIII |

TABLE I-continued
Structure and Naming of Sulfonium and Iodonium Salts*

| STRUCTURE | NUMBER |
|---|---|
| φ₂S⁺–C₆H₄–NH(CH₂)₄–N(C₆H₅)₂ PF₆⁻ | XIV |
| φ₂S⁺–φ PF₆⁻ | XV |
| φ₂S⁺–C₆H₄–OCH₃ PF₆ | XVI |
| φ–I⁺–φ PF₆⁻ | XVII |

*see examples for corresponding names of the salts
φ means phenyl
Me means methyl Tethered sulfonium salt photoinitiators of this invention are required to be soluble or dispersible in the compositions in which the initiators are employed to be effective. Sensitizers may be soluble or dispersible in the compositions, but preferably the sensitizers are soluble. By soluble is meant that at least 90 percent of the added material dissolves in the composition at the concentrations in which they are useful. Tethered electron donor/sulfonium salt, sensitizer/sulfonium salt, sensitizer/sulfonium salt/donor, and/or donor, and/or sensitizer and combinations thereof are present in "photochemically effective amounts", that is, amounts of each component sufficient to enable the monomer to undergo photochemical gelation or hardening upon exposure to light of the desired wavelength. Preferably, for every 100 parts monomer, a composition of the invention contains about 0.005 to about 10 parts (more preferably about 0.1 to 4 parts) each of tethered sulfonium salt and optionally donor and/or sensitizer.

Compositions of the invention can contain a wide variety of adjuvants depending on the desired end use. Suitable adjuvants include solvents, diluents, resins, binders, plasticizers, pigments, dyes, inorganic or organic reinforcing or extending fillers (at preferred amounts of about 10 percent to about 90 percent by weight, based on total weight of composition), thixotropic agents, indicators, inhibitors, stabilizers, UV absorbers, medicaments (e.g. leachable fluorides) and the like. Amounts and types of such adjuvants, and their manner of addition to a composition of the invention will be familiar to those skilled in the art.

Compositions of the invention should be protected from actinic radiation by appropriate shielding or filters known in the art until polymerization and cure are desired. Ingredients may be mixed in any order of addition to provide compositions of the invention. Use of an inert atmosphere such as nitrogen or argon and the like to prevent inhibition of polymerization by molecular oxygen is preferable, but this invention can also be practiced in the presence of oxygen.

Suitable temperatures for use in the polymerization of compositions of this invention are in the range of $-50°$ C. to $250°$ C., preferably $20°$ C. to $50°$ C. Compositions may be heated before, during, or after photocuring.

Photocuring free radical polymerizable compositions containing photoinitiators of this invention can be effected using photochemically effective amounts, that is, amounts of each component sufficient to cause the compositions to polymerize upon exposure to actinic radiation at wavelengths in the range of 300–700 nanometers (nm).

Polymerizable compositions of this invention can be applied to substrates by coating techniques such as dipping, bar coating, roller coating, and those coating techniques well known by those skilled in the art.

Suitable substrates on which the composition may be layered include metals such as aluminum, steel, copper, nickel and the like, polymer films such as polyesters including polyethylene terephthalate, polyvinylchloride, polyamides and polyimides, polyolefins including polyethylene and polypropylene, cellulose acetate, paper, wood, glass, and ceramics and may be flexible or inflexible. Substrates may be flat or shaped.

Compositions of the invention can be cured using a variety of methods. It is convenient to employ light sources that emit ultraviolet or visible light such as quartz halogen lamps, tungsten halogen lamps, mercury arc lamps, carbon arc lamps, low-, medium-, and high-pressure mercury lamps, plasma arc lamps, light emitting diodes and lasers. Electron beam irradiation and other curing devices that do not depend on light emission can also be employed. In general, heat and/or an inert atmosphere will accelerate cure.

In another aspect, this invention can provide a patterned article or patterned layered structure wherein at least a portion of a first side of an appropriate substrate (by appropriate substrate is meant a substrate which will allow the passage of actinic radiation and having an absorbance of less than 1.0 at the wavelengths of the actinic radiation, i.e., which are transmissive to actinic radiation such as polypropylene, polyethylene terephthalate, borosilicate glass, cellulose acetate, and the like), is first masked to provide a patterned sheet substrate having masked and unmasked surface areas. Onto at least a portion of a second side of the patterned substrate can then be coated the above polymerizable composition, which may then be polymerized by irradiating with actinic radiation through the first side of the masked substrate. Any masked, and hence unpolymerized composition can be removed, e.g., by washing with a suitable liquid in which the composition is soluble or dispersible, as is known in the art, to leave a patterned, layered structure. The patterned layered structure can be further overcoated with polymerizable and resultant polymerized compositions of this invention.

In another aspect, this invention can provide a patterned article wherein a substrate, which may be either transmissive or not transmissive to radiation, is coated with polymerizable compositions of the present invention. A mask is applied in direct contact with the polymerizable composition to provide a patterned substrate having masked and unmasked surface areas, and at least a portion of the polymerizable composition is irradiated through the mask with actinic radiation. Following irradiation and subsequent removal of the mask, any masked, and hence unpolymerized composition, can be removed, e.g., by washing with a suitable liquid, as is known in the art (e.g., for acrylate-containing composition methyl ethyl ketone, acetone, dichlormethane, tetrahydrofuran), to leave a patterned, layered structure. The patterned layered structure can be further overcoated with polymerizable, and subsequently polymerized, compositions of this invention.

In a still further aspect, this invention can provide a patterned article wherein a substrate, which may be either transmissive or not transmissive to radiation, is coated with the above polymerizable composition and a transparent protective composition is coated onto the polymerizable composition. A mask is applied in direct contact with the transparent protective coating composition to provide a patterned substrate having masked and unmasked surface areas, and at least a portion of the polymerizable composition is irradiated with actinic radiation through the mask. Following irradiation and subsequent removal of the mask and protective coating, e.g., by washing with a suitable liquid, any masked, and hence unpolymerized composition can be removed, e.g., by washing with a suitable liquid, to leave a patterned, layered structure. The patterned layered structure can be further overcoated with polymerizable, and subsequently polymerized, compositions of this invention.

Compositions of this invention are useful in protective coatings, photopolymers, graphic arts, especially in the art of printing plates, and wherever free radical polymerization of photocurable compositions is desirable.

Objects and advantages of this invention are further illustrated by the following examples, but the particular materials and amounts thereof recited in these examples, as well as other conditions and details, should not be construed to unduly limit this invention.

EXAMPLES

In the examples listed below the following abbreviations are used: tetrahydrofuran (THF), dimethyl sulfoxide (DMSO), 9,10-diethoxyanthracene (DEA), 4,4'-bis(-dimethylaminobenzylidene)acetone (DMBA). All compounds for which preparations are described in the following examples were analyzed by at least one of H nuclear magnetic resonance, fast atom bombardment mass spectroscopy, infrared spectroscopy, ultraviolet-visible spectroscopy, or a combination thereof. All reactants and reagents are commercially available (Aldrich Chemical Company, Milwaukee, WI) unless otherwise specified. As best as possible we have given a name to the compounds of Table I which are referred to in the following examples.

EXAMPLE 1

The following example describes the preparation of 4-(2',-aminoethyl)phenyldiphenylsulfonium hexafluorophosphate (I). Methanesulfonic acid (30 mL, 98%), 10 g phosphorus pentoxide, and 5.0 g diphenyl sulfoxide were mixed in a 100 mL round-bottomed (rb) flask under dry nitrogen. Phenethylamine (3.0 g), was added and the mixture was stirred with heating at 56° C. for 3 hours (hr), then poured onto 200 mL crushed ice. The mixture was washed with 200 mL ether and neutralized with 30% aqueous potassium hydroxide to pH > 10. The mixture was washed with 2×200 mL portions of ether, and 7 g ammonium hexafluorophosphate was added. The mixture was extracted into 300 mL dichloromethane. The separated organic extract was dried over anhydrous magnesium sulfate, filtered, and the filtrate was evaporated under vacuum to give 2.8 g of a slightly yellow resinous foam which was crushed to give (I) as a light yellow powder, m.p., 75°-80° C.

EXAMPLE 2

The following example describes the preparation of 4-(2'-(3''-N,N-dimethylamino)benzamidoethyl)phenyldiphenylsulfonium hexafluorophosphate (II).

The following paragraph describes the preparation of N-(2-phenylethyl)-3-(N,N-dimethylamino)benzamide which is an intermediate for the preparation of compound II.

3-Dimethylaminobenzoic acid was dissolved in 200 mL dichloromethane under dry nitrogen. Thionyl chloride (21.7 g) was added with stirring followed by 3 drops of N,N-dimethylformamide. The mixture was stirred 45 minutes (min) at room temperature then heated to reflux overnight. The mixture was cooled and 20 mL triethylamine was added followed by 18.6 g phenethylamine and allowed to stand overnight. The mixture was poured into 200 mL of a 1:1 saturated aqueous sodium carbonate/water solution and separated. The organic layer was dried over anhydrous magnesium sulfate, filtered, and the filtrate evaporated under reduced pressure to give 26.7 g of intermediate N-(2-Phenylethyl)-3-(N,N-dimethylamino)benzamide, as a light yellow solid.

The intermediate (5 g) was placed in a 100 mL rb flask with 30 mL 98% methanesulfonic acid, and 10 g phosphorus pentoxide. Diphenyl sulfoxide (3.65 g), was added with stirring under dry nitrogen at room temperature. The mixture was stirred overnight and poured into ice water, washed with 2×200 mL portions of ether, and neutralized with 30% aqueous potassium hydroxide to pH > 10. The solution was washed again with 200 mL ether, and 3.0 g ammonium hexafluorophosphate was added. The mixture was extracted with 3×50 mL portions of dichloromethane which was combined, dried over anhydrous magnesium sulfate, filtered, and the filtrate evaporated under vacuum to give a resinous foam which was crushed to give 1.4 g of (II) as a yellow powder.

EXAMPLE 3

The following example describes the preparation of diphenyl-4-(2'-oxy-N-(3"-N,N-dimethylaminopropyl)acetamido)phenylsulfonium hexafluorophosphate (III).

Phenoxyacetyl chloride (8.0 g, 47 mmol), was dissolved in 100 mL THF. N,N-3-Dimethylaminopropylamine (4.37 g, 43 mmol), was added under dry nitrogen. The mixture was stirred 1 hr and poured into water, neutralized to pH>10 with 30% aqueous potassium hydroxide (KOH), and extracted with 2×150 mL portions of dichloromethane. The separated dichloromethane layer was dried over anhydrous magnesium sulfate, filtered, and the filtrate was evaporated under reduced pressure to give 7.98 g of N-(3'-(N,N-dimethylamino)-propyl)-2-phenoxyacetamide, as a yellow liquid (74% crude yield); 10.0 g of the amide was allowed to react with diphenyl sulfoxide according to the procedure of Example 2 to give 7.7 g of (III) as a yellow powder.

EXAMPLE 4

The following example describes the preparation of diphenyl-4-(2'-oxy-N-(2,,-N,N-dimethylaminoethyl)acetamido)phenylsulfonium hexafluorophosphate (IV).

Phenoxyacetyl chloride (17.8 g) and 4.5 g N,N-dimethylaminoethylenediamine were allowed to reacted according to the procedure of Example 2 to give the amide as 12.7 g of a brown liquid; 11.6 g of this material was converted to the sulfonium salt derived from diphenyl sulfoxide according to the procedure of Example 3 to give (IV) as 4.8 g of a yellow powder.

EXAMPLE 5

The following example describes the preparation of diphenyl-4-(2'-oxy-N-(4"-N,N-dimethylaminobutyl)acetamido)phenylsulfonium hexafluorophosphate (V).

The procedure of Example 3 was repeated using 7.3 g phenoxyacetyl chloride and 5.0 g 4-N,N-dimethylamino-1-butylamine. The product was converted to the sulfonium salt using diphenyl sulfoxide according to the procedure of Example 2 to give 2.4 g of (V) as a pale yellow brittle foam.

EXAMPLE 6

The following example describes the preparation of diphenyl-4-(2'-oxy-N-(6"-N,N-dimethylaminohexyl)acetamido)phenylsulfonium hexafluorophosphate (VI).

The procedure of Example 3 was followed using 5.9 g phenoxyacetyl chloride and 5.0 g 5-N,N-dimethylamino-1-hexylamine, but using chloroform as solvent in place of THF and yielding 9.0 g of amide. The amide was converted to the sulfonium salt using diphenyl sulfoxide as described in Example 2 to give 1.9 g of (VI) as a clear colorless resin.

EXAMPLE 7

The following example describes the preparation of 4-fluorophenyldiphenylsulfonium hexafluorophosphate Diphenyliodonium hexafluorophosphate was prepared according to the method of Crivello (J. V. Crivello and J. H. W. Lam *Macromolecules* 1977, 10, 1307) and recrystallized prior to use. Diphenyliodonium hexafluorophosphate (32 g), 0.4 g copper (I) benzoate, 5.2 g 4-fluorothiophenol, and 8.8 g tri-n-butylamine were combined and heated under dry nitrogen at 120° C. for 4 hours according the procedure of Crivello and Lam (Crivello, J. V.; Lam, J. H. W. *Synth. Commun.* 1979, 9, 151). The mixture was cooled to room temperature and triturated with 200 mL ether. The residue was recrystallized from methanol to yield 6.9 g 4-fluorophenyldiphenylsulfonium hexafluorophosphate (VII).

EXAMPLE 8

The following example describes the preparation of diphenyl(4-(1,-piperidino)phenyl)sulfonium hexafluorophosphate (VIII).

Compound VII (1.0 g) was dissolved in 5 mL cyclohexane, and 1.0 g piperidine was added. The mixture was heated on a steam bath for 5 min, poured into 100 mL 5% hydrochloric acid, containing 1-2 g ammonium hexafluorophosphate,and combined with 40 mL dichloroethane. The mixture was separated and the organic layer was washed with 5% HCl, then water. The separated organic layer was dried over anhydrous magnesium sulfate, filtered, and the filtrate was evaporated under reduced pressure to yield 0.4 g of (VIII) as brown crystals.

EXAMPLE 9

The following example describes the preparation of 4-(4'-(4"-(3'''-(4''''-N,N-dimethylaminophenyl)-2'''-propenoyl)phenyl)-1'-piperazinophenyl)diphenylsulfonium hexafluorophosphate (IX).

A solution of 5 g p-piperazinoacetophenone, 3.65 5-N,N-dimethylaminobenzaldehyde, 175 mL 95% ethanol, and 0.1 g potassium hydroxide was prepared in an Erlenmeyer flask and allowed to stand at room temperature for 5 days. Solvent was removed under reduced pressure and the residue was recrystallized from methanol, to yield 3.05 g 3-(4'-N,N-dimethylamino phenyl)-1-(1'-(4"-phenyl)piperazino)-2-propenone as a yellow solid. Compound VII (1.0 g) and 1.0 g 3-(4'-N,N-dimethylaminophenyl)-1-(1'-(4',-phenyl)piperazino)-2-propenone were combined in a minimum amount of hot THF (approx. 40 mL), and heated to reflux for 1 hr. The mixture was poured into 50 mL 5% hydrochloric acid containing 5 g ammonium hexafluorophosphate. The mixture was extracted into dichloromethane which was separated and dried over anhydrous magnesium sulfate, filtered, and the filtrate was evaporated under reduced pressure to give 1.1 g of (IX) as an orange solid.

EXAMPLE 10

The following example describes the preparation of 4-(4'-(4"-acetylphenyl)-1'-piperazino)phenyldiphenylsulfonium hexafluorophosphate (X).

Compound VII (0.05 g) and 0.70 g 4'-piperazinoacetophenone were allowed to react according to the procedure of Example 8, to give 0.7 g of (X) as a yellow solid.

EXAMPLE 11

The following example describes the preparation of 4-(4'-N,N-dimethylaminobutyl)phenyldiphenylsulfonium hexafluorophosphate (XI).

Compound VII (0.83 g) and 2.3 g 3-N,N-dimethyaminobutylamine Were mixed in DMSO and allowed to react under the conditions of Example 8 to give 1.4 g of pale yellow liquid, which was a solution of (XI) in DMSO.

EXAMPLE 12

The following example describes the preparation of diphenyl-(4-(4'-methyl-'-piperazino)phenyl)sulfonium hexafluorophosphate (XII).

Compound VII (1.0 g), and 1.0 g N-methylpiperazine were allowed to react according to the procedure of Example 8 to give 0.9 g of (XII) as brown crystals.

EXAMPLE 13

The following example describes the preparation of 4-(4'-(9''-anthrylmethyl)-1'-piperazino)phenylsulfonium hexafluorophosphate (XIII).

In 20 mL of THF was dissolved 2.61 g of -chloromethylanthracene. In a separate flask 10 g anhydrous piperazine was dissolved in 60 mL THF. The two solutions were poured together and stirred at room temperature for 2 hrs. The mixture was poured into sufficient 10% aqueous sodium hydroxide to ensure a pH greater than 10. The mixture was extracted into ether which was separated and dried over anhydrous magnesium sulfate, filtered, and the filtrate was evaporated to give 2.34 g of -(piperazinomethyl)anthracene as an off-white powder. The -(piperazinomethyl)anthracene product (2.0 g) and 2.0 g of compound VII were allowed to react according to the procedure in Example 10 to give 2.4 g. of compound (XIII) as yellowish powder.

EXAMPLE 14

The following example describes the preparation of 4-(4'-(9''-carbazolyl)butylamino)phenylsulfonium hexafluorophosphate (XIV).

A mixture of 21.5 g. of 1,4-dibromobutane and 13.7 g of potassium carbazole (CTC Organics, Atlanta, GA), were stirred in 75 mL acetone under dry nitrogen, and the mixture was refluxed overnight (about 16 hrs). Hexanes (400 mL.) was added and the mixture was poured into water and extracted into ether which was separated, dried over anhydrous magnesium sulfate, filtered, and the filtrate evaporated under reduced pressure, to give 12.9 g of the monoadduct as white needles, mp 76°–7° C. 5.0 g of this material was combined with 3.8 g potassium carbazole in 30 mL N,N-dimethylformamide and heated to 90° C. for 1.5 hrs. The mixture was cooled and was poured into 200 mL ether and 200 mL brine. The ether was separated and was washed again with brine. The ether layer was dried over anhydrous magnesium sulfate, filtered, and the filtrate was evaporated under reduced pressure. The resulting oily residue was heated 45 minutes with 5 mL hydrazine hydrate in 200 mL 2-propanol. A solid precipitate formed which was removed by filtration. The filtrate was poured into ether and washed with water. The separated ether layer was extracted with 10% hydrochloric acid, and the separated aqueous layer was neutralized with 30% aqueous potassium hydroxide. A milky precipitate formed which was extracted into ether, dried over anhydrous magnesium sulfate, filtered, and the filtrate evaporated under reduced pressure. The residue was placed under high vacuum for 2 hr. 0.65 g of this residue and 1.16 g of (VII) were allowed to react under the conditions of Example 10 to give 1.6 g of (XIV) as a brown crystalline solid.

EXAMPLE 15

This example illustrates the increases in cure speed realized when an electron donor is tethered to a triphenylsulfonium salt, and shows that tethering is more effective than simple addition of high concentrations of an electron donor.

Samples were prepared according to the following procedure: 20 mg sulfonium salt was dissolved in 3.0 mL of solution A. Solution A was prepared as follows: 50 mL $1.0 \times 10^{-3}$ M 4,4'-bis(dimethylaminobenzylidene)acetone (DMBA) in acetonitrile was combined with 25 g trimethylolpropane triacrylate (Sartomer Company, West Chester, PA) and was diluted to 250 mL with 3:1 acetonitrile:water solution. The samples were sealed in test tubes with Teflonex faced septa and purged through the septa for 15 minutes with rapidly flowing nitrogen. The samples were then irradiated at a distance of 7.6 cm (3 inches) using a Kodak (Rochester, NY) 5200 carousel projector with a Sylvania (Winchester, KY), FHS (300 W, 82 V), tungsten halogen projection lamp. A sample was judged gelled if it could be inverted without movement of the contents of the tube. Triphenylsulfonium hexafluorophosphate (XV) and 4-methoxyphenyldiphenylsulfonium hexafluorophosphate (XVI) were prepared according to U.S. Pat. No. 4,451,408.

TABLE II

Photocuring Speeds of Several Tethered Sulfonium Salts

| SULFONIUM SALT | GEL TIME (in minutes) |
|---|---|
| I | 5.5 |
| III | 8.8 |
| IV | 8.1 |
| V | 6.2 |
| XV[b] | >>45 |
| XV[a,b] | 18.8 |
| XVI[b] | >>45 |
| XVI[a,b] | 36.0 |

[a]Contains 0.3 mL triethylamine
[b]Comparative
>> means much greater than

Data of TABLE II show that the sulfonium salts of the invention show faster cure speeds than compositions using untethered sulfonium salts.

EXAMPLE 16

This example demonstrates that many types of sensitizers are useful for tethered electron donor sulfonium salt photoinitiators.

Compound III was dissolved in 3 mL of a solution of 10% pentaerythritol tetraacrylate in 3:1 acetonitrile:water. Sensitizer was added. Samples were sealed in test tubes with polytetrafluoraethylene (Teflon ™) faced septa and purged through the septa for 15 minutes with rapidly flowing nitrogen. The samples were then irradiated at a distance of 7.6 cm (3 inches) using a Kodak ™ (Rochester, NY) 5200 Carousel ™ projector with a Sylvania ™ (Winchester, KY), FHS (300 W, 82 V), tungsten halogen projection lamp. A sample was judged gelled if it could be inverted without movement of the contents of the tube.

TABLE III

Photocuring Speeds of Sulfonium Salts with Different Sensitizers.[a]

| SULFONIUM SALT (mol/L) | SENSITIZER (mol/L) | GEL TIME (in minutes) |
|---|---|---|
| III (0.17 M) | DMBA[a] ($6.6 \times 10^{-5}$ M) | 4.0 |
| III (0.18 M) | perylene ($1.7 \times 10^{-5}$ M) | 3.3 |
| III (0.15 M) | DEA[b] ($4.9 \times 10^{-4}$ M) | 6.3 |

TABLE III-continued

Photocuring Speeds of Sulfonium Salts with Different Sensitizers.[a]

| SULFONIUM SALT (mol/L) | SENSITIZER (mol/L) | GEL TIME (in minutes) |
|---|---|---|
| III (0.18 M) | none[b] | 13.3 |
| XV (0.15 M)[c] | DMBA[a] (6.6 × 10$^{-5}$ M) | >400 |
| XV (0.15 M)[c] | none[b] | >20 |

[a] 435 nm cutoff filter used (GG-435, Ealing Optical, South Natick, MA)
[b] 300 nm Pyrex ™ cutoff filter used.
[c] Comparative Data of Table III show that many types of sensitizers are useful for tethered electron donor sulfonium salt photoinitiators.

EXAMPLE 17

The following example illustrates the thermal stability of tethered electron donor sulfonium salt photoinitiators compounds III and XII. Compound III (20 mg) and 20 mg compound XV (comparative) were placed in separate test tubes and dissolved in 3 mL of a solution of 10% pentaerythritol tetraacrylate in 3:1 acetonitrile: water, sealed with a Teflon ™ faced septa, and purged through the septa with nitrogen for 15 min., respectively. The tubes were heated in an oil bath at 60° C. The tube containing (XV) gelled in 12.5 minutes whereas the tube containing (III) showed no sign of gelation after 45 minutes. A differential scanning calorimeter Du Pont Model 912 (Wilmington, DE), and Du Pont Model 9900 thermal analyzer were used to determine the thermal behavior of (XII), which showed a melting point at 194°–195° C. and decomposed at temperatures above 230° C.

EXAMPLE 18

The following example illustrates utility of tethered sensitizer sulfonium salt initiators for free radical curing in solution.

A 30% (wt/vol) solution of pentaerythritol tetraacrylate (Sartomer, West Chester, PA) in 2-butanone was prepared. 4'-piperazinoacetophenone (4-PA) and various sulfonium salt initiators were added to 3 mL of this solution in test tubes sealed with Teflon faced septa and purged through the septa 15 minutes with nitrogen. Samples were irradiated according to Example 16 and the gel point was observed and are reported in TABLE IV. Note that compound XIII failed to show signs of curing and anthracene fails the criterion for a useful sensitizer cited in the inequality above.

TABLE IV

Photocuring Speeds of Tethered Sensitizer Sulfonium Salt Composition for Free Radical Cure

| SULFONIUM SALT | 4-PA (mg) | GEL TIME (seconds) |
|---|---|---|
| X (25 mg) | 0 | 113 |
| VIII (20 mg) | 8.3 | 222 |
| none[a] | 8.3 | 331 |
| XV (17 mg)[a] | 8.3 | 225 |
| XIII (25 mg)[a] | 0 | >1800 |

[a] Comparative

EXAMPLE 19

The following example illustrates the usefulness of tethered sensitizer sulfonium salt photoinitiators for free radical curing in films.

Solution (B) was prepared by adding 0.025 g (X) to 3.0 mL of a solution of pentaerythritol tetraacrylate in THF (30% wt/vol). A solution (C) was prepared by adding 0.016 g XV and 0.025 g (3 equivalents), of 4'-piperazinoacetophenone (4-PA) to 3.0 mL of a solution of pentaerythritol tetraacrylate in THF (30% wt/vol). Solutions B and C, respectively, were coated onto separate polyvinylidene chloride primed polyester sheet (3M Company, St. Paul, MN) using a #20 Meyer Bar (R&D Specialities, Webster, NY) to give a coating thickness of approximately 370 mil. Each sample in turn, was cut in half lengthwise and laminated together such that both coated sides were in contact, and then rolled by hand with an ink roller to remove air bubbles. The samples were then irradiated through a Stouffer 21 step sensitivity guide (transmission density 0.15/step, Stouffer Graphic Arts Equipment, South Bend, IN), under two General Electric F15T8/BLB bulbs at a 5 cm (2 inch) distance. Following irradiation the composite was peeled apart and briefly rubbed with a cotton ball. The residue remaining after this procedure was observed and the number of solid steps was recorded. A patterned article was formed. The following table (V) indicates the results.

TABLE V

| SOLUTION | STEPS |
|---|---|
| B | 7 |
| C (comparative) | 6 |

Data of TABLE V show that a tethered sensitizer sulfonium salt initiator (B) provided higher speed and greater sensitivity than a comparative composition (C) with untethered sulfonium salt.

EXAMPLE 20

This example demonstrates utility of compound IX as a photoinitiator for free radical polymerization in A 10% (wt/vol) solution of pentaerythritol tetraacrylate in 2-butanone was coated using a #20 Meyer bar and laminated together as described in Example 20 and irradiated for 20 seconds in a 3M Model 70 Transparency Maker (3M Company, St.Paul, MN). After development according to Example 20 six solid steps were observed. A patterned article was provided.

EXAMPLE 21

The following example demonstrates the high temperature stability of tethered sensitizer sulfonium salt initiators.

A differential scanning calorimeter Du Pont Model 912 (Wilmington, DE), and Du Pont Model 9900 thermal analyzer were used to determine the thermal behavior of sulfonium salts. Compound IX showed decomposition above 185° C. Compound X melted at approximately 240° C., and compound XIII showed no sign of melting or decomposition up to 270° C.

EXAMPLE 22

The following example illustrates the usefulness of tethered sensitizer sulfonium salt initiators for free radical curing in solution.

Compound XIV (33 mg) was dissolved in 3 mL of a solution of pentaerythritol tetraacrylate in 3 : 1 acetonitrile water, sealed in a test tube, and purged 10 minutes with nitrogen. A second tube was prepared in the same manner using 10 mg N-ethylcarbazole and 30 mg VIII instead of XIV. Both tubes were irradiated according to Example 16. The first tube gelled in 5.75 min while the second tube took 10.75 min to gel.

EXAMPLES 23 to 25

The following examples illustrate the usefulness of tethered sensitizer sulfonium salt initiators for free radical curing in solution.

EXAMPLE 23

Compound XIV (33 mg) was dissolved in 3 mL of a solution of pentaerythritol tetraacrylate in 3 : 1 acetonitrile:water, sealed in a test tube with a Teflon faced septum, and purged through the septum 10 minutes with nitrogen. A second tube was prepared in the same manner using 10 mg N-ethylcarbazole and 30 mg (VIII) instead of (XIV). Both tubes were irradiated according to Example 16. The first tube gelled in 5.75 min while the second tube took 10.75 min to gel.

EXAMPLE 24

A solution of 20 g pentaerythritol tetraacrylate in 80 g 2-butanone was prepared (solution D). 3.0 mL of solution D and 50 mg (IX) were combined in a test tube fitted with a Teflon faced septum and purged through the septum for 10 minutes with dry nitrogen. The mixture was irradiated as described in Example 16. The mixture gelled in 570 seconds.

EXAMPLE 25

Solution D (85 mL) from Example 24 was mixed with 0.100 mL triethylamine (solution E). 50 mg IX was added to 3.0 mL solution D as described in a test tube fitted with a Teflon faced septum and purged through the septum for 10 minutes with dry nitrogen. The mixture was irradiated as described in Example 16. The mixture gelled in 400 seconds.

Various modifications and alterations of this invention will become apparent to those skilled in the art without departing from the scope and spirit of this invention, and it should be understood that this invention is not to be unduly limited to the illustrative embodiments set forth herein.

We claim:

1. A free radical polymerizable composition comprising an ethylenically unsaturated monomer, at least one of an electron donor and a sensitizer, and a triarylsulfonium salt, wherein at least one of said electron donor and sensitizer is tethered with said sulfonium salt through at least one tetracoordinate carbon atom which is bonded to four separate substituents.

2. The free-radical polymerized composition according to claim 1 wherein said tethered sulfonium salt has a formula selected from formulae (1) and (2) wherein Formula (1) is:
$S^+(A^1)_m(A^2-T$ 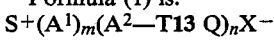 $Q)_n X^-$ wherein $S^{30}$ is a positively charged sulfur atom,
$A^1$ is an aryl or substituted aryl group having 6 to 50 carbon atoms,
$A^2$ is an arylene group having 6 to 50 carbon atoms, which is connected to Q through a tether T,
m32 0, 1, or 2; n32 1, 2, or 3: with the proviso that n30 m32 3,
Q represents an electron donor,
T represents the tether which joins the triarylsulfonium slat moiety and Q and contains at least one tetracoordinate carbon atom which is bonded to four separate substituents,
  with the proviso that every path from $A^2$ to Q contains at least one tetracoordinate carbon atoms; and
X is a counterion, Formula (2) is:

$(Q\rightarrow T)_k A^2 S^+ A^3 -(T-Q)_j X^-$ 

wherein $S^{30}$, $A^2$, T, Q and $X^-$ are as previously defined,
j=0, 1, 2, 3, or 4,
k=0, 1, or 2,
$A^3$ is a polycyclic group having 1 to 40 carbon atoms comprising at least two distinct fused or single phenyl rings, wherein both phenyl rings are singly and individually bonded to $S^+$.

3. The composition according to claim 2 wherein said salt has the formula

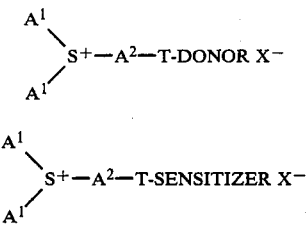

wherein $S^+$, $A^1$, $A^2$, T, and $X^-$ are as previously defined, DONOR is an electron donor and SENSITIZER is a photosensitizer.

4. The composition according to claim 1 wherein said monomer contains at least one ethylenically unsaturated double bond.

5. The composition according to claim 4 wherein said monomer is at least one mono-, di-, or polyacrylate or methacrylate.

6. The composition according to claim 1 wherein said donor contains an electron donor atom selected from the group consisting of N, O, P, and S.

7. The composition according to claim 1 wherein said donor is an amine, amide, or urea.

8. The composition according to claim 1 wherein said composition comprises both an electron donor and sensitizer.

9. The composition according to claim 8 wherein said electron donor is tethered to said sulfonium salt and said sensitizer is a separate molecule.

10. The composition according to claim 8 wherein said sensitizer is tethered to said sulfonium salt and said electron donor is a separate molecule.

11. The composition according to claim 8 wherein said sulfonium salt, said electron donor, and said sensitizer are in the same molecule.

12. The composition according to claim 8 wherein $E_{ox} - E_{o,o}$ for the sensitizer is in the range of $-1.5$ to $-4.5$ electron V (vs. S.C.E.) wherein $E_{o,o}$=the energy of the lowest excited state and $E_{ox}$=the oxidation potential of the sensitizer.

13. The composition according to claim 2 wherein T is chosen from divalent groups selected from the group consisting of alkylene, aminoalkylene, aralkylene, alkarylene, haloalkylene, thioalkylene, and oxyalkylene, wherein the divalent group contains 1 to 40 C atoms, and none or 1 to 10 N, 0, S, P, Si, and Se heteroatoms, and optionally contains amide, ester, ether, or ketone functionality.

14. A layered structure comprising a substrate and having on at least a portion of at least one surface thereof a layer of the composition according to claim 1.

15. The layered structure according to claim 14 wherein said composition is cured.

16. A method for providing a patterned layered structure comprising the steps:

(a) providing a substrate which is transmissive to actinic radiation having a pattern on a first surface thereof, (b) coating on at least a portion of the second surface of said substrate a layer of the composition according to claim 1, (c) subjecting said first surface to actinic radiation for a time sufficient to polymerize said composition, (d) washing said second surface with a liquid suitable for removing unpolymerized composition in patterned areas to provide a patterned layered structure.

17. The cured layered structure according to claim 15 wherein said composition contains residual triarylsulfonium salt.

* * * * *